United States Patent
Westfechtel et al.

(10) Patent No.: US 6,548,717 B1
(45) Date of Patent: Apr. 15, 2003

(54) PROCESS FOR MAKING BRANCHED, SUBSTANTIALLY UNSATURATED FATTY ALCOHOLS

(75) Inventors: Alfred Westfechtel, Hilden (DE); Norbert Huebner, Duesseldorf (DE); Lothar Friesenhagen, Duesseldorf (DE); Gerrit Pelzer, Duesseldorf (DE); Norbert Klein, Mettmann (DE); Ansgar Behler, Bottrop (DE); Thomas B. Downing, Duesseldorf (DE); Steven A. Kennedy, Cincinnati, OH (US); C. William Blewett, Lakeside Park, KY (US)

(73) Assignee: Cognis Deutschland GmbH & Co. KG, Duesseldorf (DE)

( * ) Notice: Subject to any disclaimer, the term of this patent is extended or adjusted under 35 U.S.C. 154(b) by 0 days.

(21) Appl. No.: 09/602,988

(22) Filed: Jun. 23, 2000

Related U.S. Application Data

(60) Provisional application No. 60/141,150, filed on Jun. 25, 1999.

(51) Int. Cl.$^7$ ................................................. C07C 27/04
(52) U.S. Cl. ........................................ 568/885; 568/884
(58) Field of Search ........................... 568/884, 885, 568/892; 554/224, 124, 126, 127, 128, 159

(56) References Cited

U.S. PATENT DOCUMENTS

| | | |
|---|---|---|
| 3,193,586 A | 7/1965 | Rittmeister et al. |
| 3,729,520 A | 4/1973 | Rutzen et al. |
| 5,672,781 A | * 9/1997 | Koehler et al. ............. 568/885 |

FOREIGN PATENT DOCUMENTS

| | | | | |
|---|---|---|---|---|
| DE | 4335781 | 10/1993 | | |
| EP | 0602108 | 1/1996 | | |
| GB | 1146207 A | * 3/1969 | ........... | C07C/57/60 |
| JP | 08301822 | * 11/1996 | | |

OTHER PUBLICATIONS

A. Behr et al., "Katalytische Oligomerisierung von Fettstoffen", *Fat Sci. Technol.* 93, pp. 340–345 (1991).

H. Moehring et al., "Produkte der Dimerisierung ungesaettigter Fettsaeuren VII: Kinetische Untersuchung der Mono– und Dimeren, die bei der Dimerisierung von Oelsaeure entstehen", *Fat Sci. Technol.* 94, 41–46 (1992).

H. Moehring et al., "Produkte der Dimerisierung ungesaettigter Fettsaeuren VIII: Ueber die Zusammensetzung der Fraktion der "Intermediates" bei der Fettsaeuredimerisierung", *Fat Sci. Technol.* 94, 241–245 (1992).

* cited by examiner

Primary Examiner—Johann Richter
Assistant Examiner—Elvis O. Price
(74) Attorney, Agent, or Firm—John E. Drach; Steven J. Trzaska

(57) ABSTRACT

A process for making branched, substantially unsaturated fatty alcohols involving: (a) providing a $C_{16-22}$ fatty acid; (b) dimerizing the $C_{16-22}$ fatty acid to form a monomer fraction containing branched, substantially unsaturated fatty acids; (c) removing the monomer fraction; (d) esterifying the branched, substantially unsaturated fatty acids contained in the monomer fraction into branched, substantially unsaturated fatty acid methyl esters; and (e) hydrogenating the branched, substantially unsaturated fatty acid methyl esters with their double bonds intact, to form the branched, substantially unsaturated fatty alcohols.

6 Claims, No Drawings

PROCESS FOR MAKING BRANCHED, SUBSTANTIALLY UNSATURATED FATTY ALCOHOLS

CROSS-REFERENCE TO RELATED APPLICATIONS

This application claims priority from U.S. provisional application Ser. No. 60/141,150 filed Jun. 25, 1999, the disclosure of which is incorporated herein by reference.

BACKGROUND OF THE INVENTION

Field of the Invention

This invention relates generally to oleochemical raw materials and, more particularly, to unsaturated fatty alcohols which, through the presence of branches in the hydrocarbon chain, are distinguished from linear homologs by significantly improved properties, to a process for their production and to their use for the production of surface-active compositions.

Unsaturated fatty alcohols, which are largely obtained from beef tallow by hydrolysis of the triglycerides, roll-up separation of the fatty acids into the substantially saturated stearin fraction and the predominantly unsaturated olein fraction, esterification of the olein and subsequent hydrogenation of the methyl ester with the double bonds intact, are important raw materials both for the production of cosmetic preparations and for the production of laundry detergents, dishwashing detergents and cleaning compositions. Thus, the alcohols themselves are used for example as concrete parting agents, their derivatives, for example ethoxylates, sulfates and ether sulfates, are used as emulsifiers or surfactants in shampoos and liquid detergents and oleyl esters are frequently used as cosmetic oil components. The favorable properties of these substances are linked to the presence of the double bond in the molecule although this also presents problems because the unsaturated fatty alcohols readily fall victim to auto-oxidation which is associated with discoloration and unwanted chemical changes (for example formation of peroxides and hydroperoxides).

Accordingly, it is clear that there is a need on the market for unsaturated fatty alcohols with improved oxidation stability or suitable substitutes which possess at least equivalent performance properties. However, more or less pure isostearyl alcohols have hitherto been the only alternatives to unsaturated fatty alcohols. To produce them, oleic acid first has to be dimerized, the fraction of monomeric branched fatty acids separated off, hydrogenated and subjected to fractional crystallization, the liquid fraction accumulating, which is rich in isostearic acid, has to be removed and esterified with methanol and the esters obtained subsequently hydrogenated to form the alcohols.

The process described above is technically complicated by the two hydrogenation steps and, in the isostearyl alcohols, provides substitutes which can only replace the unsaturated fatty alcohols to a limited extent. Accordingly, the problem addressed by the present invention was to provide unsaturated fatty alcohols which would be distinguished by improved oxidation stability for at least comparable performance properties.

Description of the Invention

The present invention relates to branched, substantially unsaturated fatty alcohols which are obtainable by (a) dimerizing unsaturated $C_{16-22}$ fatty acids in known manner, (b) removing the monomer fraction accumulating in the dimerization step, (c) converting the branched, substantially unsaturated fatty acids present in this fraction into the corresponding fatty acid methyl esters and (d) hydrogenating the branched, substantially unsaturated fatty acid methyl esters with the double bonds intact.

It has surprisingly been found that the branched, substantially unsaturated fatty alcohols have distinctly improved auto-oxidation stability compared with linear homologs having the same chain length and the same iodine value.

Production of the Substantially Unsaturated Fatty Alcohols

The present invention also relates to a process for the production of branched, substantially unsaturated fatty alcohols in which (a) unsaturated $C_{16-22}$ fatty acids are dimerized in known manner, (b) the monomer fraction accumulating in the dimerization step is removed, (c) the branched, substantially unsaturated fatty acids present in this fraction are converted into the corresponding fatty acid methyl esters and (d) the branched, substantially unsaturated fatty acid methyl esters are hydrogenated with the double bonds intact.

The dimerization of fatty acids and the recovery of monomer fatty acids from the dimers is sufficiently well-known from the prior art, cf. for example the overviews by A. Behr et al. [*Fat Sci. Technol.* 93, 340 (1991)] and by H. Möhring et al. [ibid. 94, 41 (1992) and 94, 241 (1992)]. The sequence of steps (a) to (d) gives branched, substantially unsaturated fatty alcohols with iodine values of 45 to 85 on the basis of dimerized, preferably monounsaturated $C_{16-22}$ fatty acids, i.e. oleic acid, elaidic acid, petroselic acid, gadoleic acid and erucic acid and mixtures thereof. This is without doubt entirely adequate for a number of applications. However, in cases where fatty compounds with a relatively high content of unsaturated compounds are required, it is advisable to subject the monomer fraction accumulating in the dimerization step to fractional crystallization and then to subject the liquid phase obtained to esterification, optionally after distillation. The fatty acid obtained and its methyl esters represent an already fairly pure isooleic acid or isooleic acid methyl ester with iodine values of 75 to 95. In any event, it is advisable to subject the methyl esters and/or the fatty alcohols to distillation and/or fractional crystallization ("winterizing"). The esterification of the fatty acids with methanol is carried out by known methods and is intended to produce methyl esters which are comparatively easy to hydrogenate. Instead of the methyl esters, other lower alkyl esters, for example ethyl, propyl or butyl esters, may of course also be produced and subsequently hydrogenated. The choice of the alcohol is basically not critical and is solely determined by economic criteria and availability. Instead of the methyl or lower alkyl esters, it is also possible in principle directly to esterify the fatty acids, although this does involve the use of special catalysts which do not form salts with the acids. In addition, the reactor material has to be corrosion-resistant. The hydrogenation of the unsaturated methyl esters to form the corresponding alcohols may also be carried out in known manner. Corresponding processes and catalysts, particularly those based on copper and zinc, are disclosed for example in the following documents: DE 43 357 81 C1, EP 0 602 108 B1, U.S. Pat. No. 3,193,586 and U.S. Pat. No. 3,729,520 (Henkel); reference is expressly made to the disclosures of these documents.

Commercial Applications

The new branched substantially unsaturated fatty alcohols are distinguished by particular stability to oxidation and are therefore suitable for the production of surface-active compositions, preferably laundry detergents, dishwashing detergents, cleaners and softeners, and cosmetic and/or pharmaceutical preparations in which they may be present in quantities of 1 to 50% by weight, preferably 5 to 35% by weight and more preferably 10 to 25% by weight.

EXAMPLES

Example 1

23 kg of the monomer fatty acid Edenor® 935 (Henkel KGaA) were esterified with 20 kg of methanol for 2 h at 240° C./100 bar. After removal of the water/methanol mixture, the same quantity of fresh methanol was added and the procedure was repeated twice. The ester thus obtained had an acid value of 0.8. The methyl ester was hydrogenated on a fixed-bed Zn/Cr catalyst with the double bond intact. The throughput of methyl ester was 0.5 unit by volume per hour, based on the total volume of the reactor. After removal of the methanol, the crude alcohol was distilled (3% first runnings, 90% main runnings, 6% residue). The resulting alcohol had a hydroxyl value of 192, a saponification value of 0.9 and an iodine value of 74 (solidus point 25.8° C.).

Example 2

Monomer fatty acid was substantially freed from straight-chain saturated fatty acids by crystallization from methanol/water (Emersol process). Around 20% by weight of fatty acid, predominantly palmitic and stearic acid, was removed in this way. The liquid fatty acid mixture obtained after removal of the solvent by distillation had a titer of 5° C. and was first converted into the methyl ester and then hydrogenated to the unsaturated fatty alcohol in the same way as in Example 1. The unsaturated fatty alcohol had a hydroxyl value of 191, a saponification value of 1.7 and an iodine value of 87 (solidus point 3.8° C.).

Example 3 and Comparison Example C1

The auto-oxidation stability of the new branched, substantially unsaturated fatty alcohols was tested by the standard method AOCS CD12B92. The alcohol of Example 2 remained stable for more than 90 h whereas a linear unsaturated fatty alcohol with the same iodine value (HD Ocenol 80/85 V) remained stable for only 10 hours under the same conditions.

What is claimed is:

1. A process for making branched, substantially unsaturated fatty alcohols comprising:
    (a) providing an unsaturated $C_{16-22}$ fatty acid;
    (b) dimerizing the unsaturated $C_{16-22}$ fatty acid to form a monomer fraction containing branched, substantially unsaturated fatty acids;
    (c) removing the monomer fraction;
    (d) esterifying the branched, substantially unsaturated fatty acids contained in the monomer fraction into branched, substantially unsaturated fatty acid methyl esters; and
    (e) hydrogenating the branched, substantially unsaturated fatty, acid methyl esters with their double bonds intact, to form the branched, substantially unsaturated fatty alcohols.

2. The process of claim 1 further comprising fractionally crystallizing the monomer fraction of (c) in order to obtain a liquid phase containing the branched, substantially unsaturated fatty acids prior to esterification.

3. The process of claim 2 further comprising distilling the liquid phase prior to esterification.

4. The process of claim 1 further comprising distilling the branched, substantially unsaturated fatty alcohols.

5. The process of claim 1 further comprising fractionally crystallizing the branched, substantially unsaturated fatty alcohols.

6. The process of claim 1 wherein the branched, substantially unsaturated fatty alcohols have an iodine value of from 45 to 85.

* * * * *